United States Patent

Schapira et al.

Patent Number: 6,028,226
Date of Patent: Feb. 22, 2000

[54] PROCESS FOR 3,4-DISUBSTITUTED DINITROANILINES

[75] Inventors: Joseph Schapira, Paris; Jean-Claude Cheminaud, Herblay; Jean-Jacques Gasse, Gaillon; Vincent Schanen, Paris; Benoit Rondot, Levallois Perret; Jean-Claude Lemoine, Chatnay Malabry, all of France

[73] Assignee: Cfpi Agro, Gennevilliers, France

[21] Appl. No.: 09/056,415

[22] Filed: Apr. 7, 1998

[30] Foreign Application Priority Data

Apr. 7, 1997 [FR] France ................................. 97 04235
Jul. 2, 1997 [FR] France ................................. 97 08359

[51] Int. Cl.[7] ................................................. C07C 213/00
[52] U.S. Cl. ............................................................ 564/399
[58] Field of Search ............................................. 504/399

[56] References Cited

U.S. PATENT DOCUMENTS 5,475,148  12/1995  Sarel .

FOREIGN PATENT DOCUMENTS 0 630 883  6/1994  European Pat. Off. .
WO 97 01527  6/1996  WIPO .

Primary Examiner—Samuel Barts
Attorney, Agent, or Firm—Jones & Askew, LLP

[57] ABSTRACT

Preparation process for 3,4-disubstituted dinitroanilines of formula

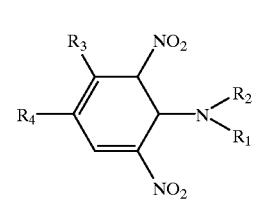

(I)

in which, $R_1$ and $R_2$, which are identical to or different from one another, represent a hydrogen atom, a $C_1$ to $C_6$ saturated, linear or branched alkyl radical, a $C_2$ to $C_6$ linear or branched alkylene radical, a cyclopropyl radical or a chloroethyl radical, $R_3$ and $R_4$, which are identical to or different from one another are chosen from the group containing the chlorine atom, the amino group, the $C_1$ to $C_3$ lower alkyl radicals and the trifluoromethyl radical, comprising successively a dinitration stage of a 3,4-disubstituted phenol, an alkylation stage of the dinitrated derivative thus obtained and an amination stage of the 3,4-disubstituted 2,6-dinitro-alkoxybenzene thus obtained.

12 Claims, No Drawings

PROCESS FOR 3,4-DISUBSTITUTED DINITROANILINES

A subject of the invention is a preparation process for 3,4-disubstituted dinitroanilines.

The dinitroanilines in question, which are known herbicides act essentially as cell division inhibitors.

They are represented by the formula

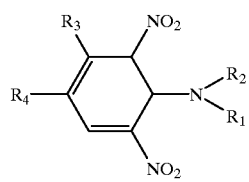

(I)

in which $R_1$ and $R_2$, which are identical to or different from one another represent a hydrogen atom, a $C_1$ to $C_6$ saturated, linear or branched alkyl radical, a $C_2$ to $C_6$ linear or branched alkylene radical, a cyclopropyl radical or a chloroethyl radical, $R_3$ and $R_4$, which are identical to or different from one another, are chosen from the group containing the chlorine atom, the amino group, the $C_1$ to $C_3$ lower alkyl radicals and the trifluoromethyl radical.

Particularly useful 3,4-disubstituted dinitroanilines are pendimethalin, prodiamine and dinitramine represented respectively by the formulae:

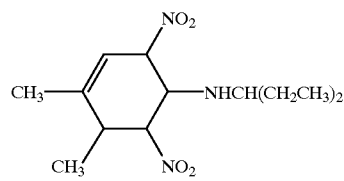

(II)

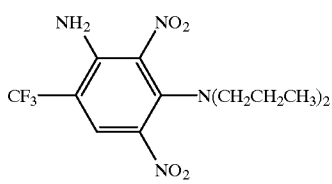

(III)

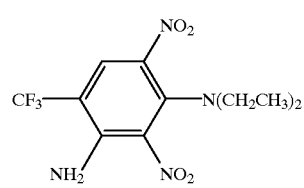

(IV)

It has already been proposed, in Patent U.S. Pat. No. 5,475,148, to prepare pendimethalin and more generally the N-alkyl-3,4dialkyl-2,6dinitroanilines by proceeding successively:

with the dinitration of 3,4-dialkylphenol using nitric acid in a diphasic medium, with the alkylation of 2,6-dinitro-3,4-dialkylphenol obtained in the previous stage preferentially in the presence of a phase transfer catalyst, with the reaction of 3,4-dialkyl-2,6-dinitro-alkoxybenzene formed in the previous stage with an amine in the presence of a catalytic quantity of base or halide.

This process is not competitive in particular due to the very poor yield at the dinitration stage.

Moreover, it is limited to the preparation of 3,4-dialkyl-substituted dinitroanilines.

Above all the aim of the invention is to overcome this drawback and to provide a preparation process for dinitroanilines disubstituted in positions 3 and 4, in an identical or different fashion, by $C_1$ to $C_3$ lower alkyl radicals, the trifluoromethyl radical, the amino group or the chlorine atom, the yield of which is compatible with practical requirements.

Now, the Applicant company has found, as a result of extensive research, that this aim can be achieved by implementing a process including successively, a dinitration stage of a 3,4-disubstituted phenol, an alkylation stage of the dinitrated derivative thus obtained and an amination stage of 3,4-disubstituted 2,6-dinitro-alkoxybenzene thus obtained and characterized in that;

the dinitration stage of the 3,4-disubstituted phenol corresponding to the sought 3,4-disubstituted dinitroaniline is carried out in a reaction medium containing a slight excess of nitrating agent, a sufficient quantity of protons and a catalyst chosen from the group containing the soluble salts of the transition metals of columns IV to XII Of the Periodic Table, preferably the soluble salts of $Fe_{III}$, $Fe_{II}$, $Zn_{II}$ and $Cu_{II}$ ions and that an O-alkylation stage of the dinitrated 3,4-disubstituted phenol obtained in the preceding stage, is carried out using an alkylating agent chosen from the group containing on the one hand, linear or branched alkyl mono-halides having at least 3 carbon atoms and which can include a saturate ring or at least one unsaturation, on the other hand, linear or branched alkyl polyhalides having at least 2 carbon atoms and which can contain a saturated ring or at least one unsaturation or yet again, polyalkoxy-haloalkyl ethers represented by the formula $(RO)_n R'X$ in which X represents a hydrogen, chlorine, bromine or iodine atom and R and R', independently of one another, represent a methyl, ethyl or propyl radical, n being such that the number of carbon atoms of the alkylating agent is $\geq 2$, in particular chloromethyl polymethoxy ethers and chloromethyl-polyethoxy ethers, the oxides of ethylene and propylene and, yet again, compounds with a structure corresponding to the formula

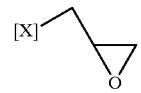

which represents epihalohydrins when X represents Cl or Br, glycidol when X represents OH, glycidyl ethers when X represents OR, R being an aliphatic chain with at most 12 carbon atoms, or an oxirane when X is an aliphatic chain R with 1 to 12 carbon atoms.

According to an advantageous embodiment of the aforesaid process, the catalyst employed during the dinitration stage is chosen from the group containing ferric and ferrous chlorides, zinc and cupric chlorides, ferric, zincic and cupric nitrates as well as ferrous, ferric, zincic and cupric sulphates.

The proportion of catalyst relative to phenol is 1 to 50 per thousand, preferably 5 to 30 per thousand.

The nitrating agent is chosen from the group containing nitric acid and water-soluble alkaline and alkaline-earth nitrates.

The excess of nitrating agent used for the dinitration stage is advantageously from about 10% to 30% by weight.

The quantity of protons which must be present in the nitrating medium is from 2 to 7, preferably from 2.4 to 6 and more preferably still, from 2.6 to 2.9 equivalents relative to the phenol and can be provided by an acid called a co-acid and constituted by an inorganic acid chosen from the group containing hydrochloric, hydrobromic, sulphuric and phosphoric acids or by an organic acid chosen from the group containing lower carboxylic acids, in particular acetic, propionic and oxalic acids.

The nitration stage can be carried out in a homogeneous nitric medium or in the presence of an inert solvent.

The inert solvent is chosen advantageously from the group containing aliphatic alkanes, in particular hexane, heptane, octane, nonane and dodecane, chlorinated derivatives, in particular dichloromethane, 3,2-dichloroethane, chloroform, trichloroethylene, tetrachloroethylene and dialkyl-ethers, in particular diethyl- and dipropyl-ethers as well as dibutyl-ethers.

The reaction is advantageously carried out under atmospheric pressure and at temperatures from −20° C. to +80° C.

The 2,6-dinitrated derivative obtained can be separated and purified by standard techniques which are well known to a person skilled in the art.

When the nitration stage is carried out without solvent, the dinitrated derivative is precipitated by dilution and ice-cooling of the reaction medium, then separated by filtration. Conversely, when the nitration stage is carried out in a solvent, the dinitrated derivative solubilized in the organic phase is isolated by decanting, the nitrating agent contained in the aqueous phase can then be recycled to the nitration stage once it has undergone concentration.

The purity of the 4-substituted 2,6-dinitrophenol derivative obtained is generally excellent and further purification is not required.

When the solvent is chosen judiciously, it does not become necessary to isolate the dinitrophenol and the solvent-containing solution can then be directly subjected to the following stage; for example, this is the case when the solvent is a halogenated solvent chosen from the group containing methylene chlorides, 1,2-dichloroethane, 1,2-dibromoethane, chloropropane, isopropyl chloride, isopropyl bromide, butyl chlorides, 1,2-dichloropropane and 1,2-dibromopropane.

The yield for the dinitration stage is at least 92% and can reach 99%.

According to another advantageous embodiment of the process according to the invention, the alkylating agent used during the alkylation stage is either an alkyl monohalide represented by the formula $C_nH_{2n-1}X$ in which X is a chlorine, bromine or iodine atom and n is $\geq 3$, or an alkyl polyhalide represented by the formula $C_nH_{2n-m}X_{2+m}$ in which X is a chlorine, bromine or iodine atom and n is $\geq 2$ with $0<m\leq 2n$.

The alkylating agent can be chosen from the group containing:

as alkyl monohalides, n-propyl, isopropyl, n-butyl, sec-butyl, isobutyl, tertbutyl, n-pentyl, sec-amyl, 3-pentyl, neopentyl, hexyl, isohexyl, cyclohexyl, cyclopropyl, benzyl, allyl halides and polyalkoxyalkyl halides with a methoxy, ethoxy or propanoxy radical as the alkoxylated chain, as alkyl polyhalides, the dihaloethanes, in particular dichloroethane and dibromoethane, the dihalopropanes, in particular 1,2- and 1,3-dichloropropanes.

The reaction conditions for the etherification of the dinitrophenols are well known to a person skilled in the art.

In general, these reactions are carried out on the dinitrated phenol or on the corresponding alkaline phenate in aqueous medium or more advantageously in biphasic medium by phase transfer reaction.

The alkaline phenate can be a dinitrophenate either of sodium or potassium, or of an organic salt such as ammonium, the quaternary tetra-alkyl ammoniums and the quaternary tetra-alkyl phosphoniums.

The alkylating agent, in solution in a solvent which is immiscible with water, is mixed with an aqueous solution of the alkaline phenate in the presence of a phase transfer catalyst which can be constituted by ammonium halide or a quaternary phosphonium salt.

The solvent can be chosen from the group containing aromatic solvents, aliphatic alkanes and ketones; preferably it is chosen from the group containing toluene, O-xylene, m-xylene, p-xylene, hexane, heptane, octane, nonane, dodecane, methylethyl ketone, methylisobutyl ketone, cyclohexanone and mixtures of these solvents.

It is also possible for an excess of alkylating agent to be used as solvent.

The preferred catalysts are tetrabutylammonium chloride, tetrabutylammonium bromide, tetrabutylphosphonium bromide, triethylbenzylammonium chloride, trimethylbenzylammonium.

The alkylation reaction can be carried out at a temperature from 15° C. to 150° C., under atmospheric pressure or under a pressure of up to 15 bars.

The phase transfer reactions can be carried out at temperatures which vary from −10° C. to +50° C. and at atmospheric pressure whereas the reactions using lower alkyl halides can be carried out under a pressure of several tens of bars.

The dinitrated phenoxy-ether obtained at the end of this stage can be isolated from the reaction medium by techniques known to a person skilled in the art, such as for example extraction with an appropriate solvent or alternatively concentration followed by fractionation of the organic phase when the process uses a phase transfer reaction.

When an excess of alkylating agent is used as the solvent, the product is isolated by solubilization of the water-soluble salts, a second alkaline washing makes it possible to solubilize the unreacted dinitrophenate; back-extraction in acid medium, of the product resulting from this second washing then leads to a solution of dinitrophenol which can be easily recycled in a subsequent etherification operation.

The organic phase isolated after the second washing is subjected to evaporation of the excess of alkylating agent which can be re-used advantageously in the following operation.

However, when the solvent is chosen from the group containing toluene, xylene, aliphatic alkanes such as heptane, octane, nonane, decane and dodecane, the fractionation is not required and the organic solution obtained at this stage can be subjected to the amination stage directly.

The amination stage is carried out by reacting, under atmospheric pressure and at reflux temperature of the medium, the product of the alkylation stage with an excess of secondary or primary amine chosen from the group containing amino-3-pentane, N,N-diethylamine, N,N-dipropylamine, N-ethyl-,N-butylamine, N-propyl,N-methyl-cyclopropylamine, N-(2-chloroethyl), N-propylamine, N-propyl,N2-methyl-2methyl-2-propenylamine, N-ethyl,N-2-methyl-2-propenylamine in an inert solvent chosen from the group containing alcohols and aromatic solvents.

Preferably, an excess of amine is used which can exceed 9 moles of amine for 1 mole of product obtained in the alkylation stage.

In a completely surprising fashion the process according to the invention allows very high yields to be achieved, above 96%, without producing more than 1 ppm of N-nitrosamines and without risk of formation of explosive products.

The successive stages of the process according to the invention are in the following reaction diagram:

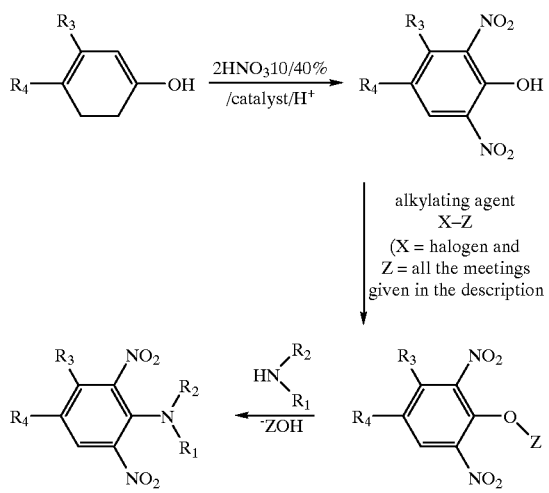

When the alkylating agent is polyfunctional, i.e. constituted for example by a dihaloethane, it is capable of reacting with two molecules of dinitrophenol and a polyetherification takes place illustrated by the reaction diagram.

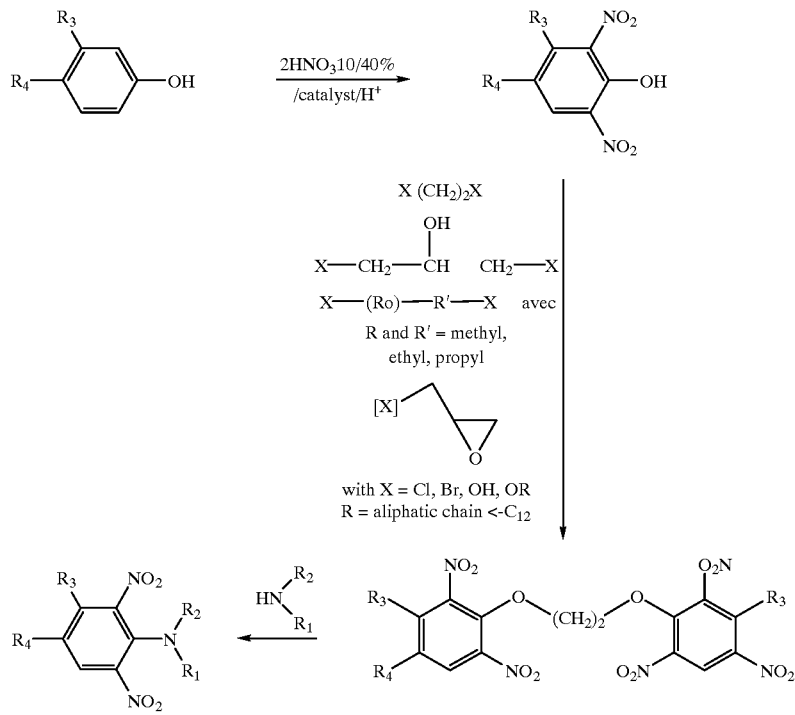

The invention will be easily understood from the following non-limitative examples, some of which relate to advantageous embodiments.

Example 1 to 9 illustrate the dinitration stage of the 3,4-disubstituted phenol.

EXAMPLE 1

This example illustrates the dinitration stage of 3,4-disubstituted phenol.

Within the space of 20 minutes and maintaining the temperature at 20° C. a solution of 4.5 g (35.7 mmol) of 3,4-dimethyl-phenol in 40 g of 1,2-dichloroethane is introduced into a nitrating medium constituted by a mixture of 23.1 g (93 mmol) of 25.5% nitric acid and 7.0 g of 37% hydrochloric acid (71 mmol); furthermore, this nitrating medium contains 80 mg of zincic-chloride.

The excess of nitrating agent is 30% and the quantity of protons present corresponds to 164 mmol, namely 4.6 equivalents relative to the phenol.

The reaction medium is left to react for two hours 30 minutes at a temperature of 50° C.

The phases are separated by decanting, the aqueous phase is extracted twice with 20 g of dichloroethane and the organic phases are combined, dried over magnesium sulphate and evaporated to dryness.

6.88 g of a yellow-orange coloured solid is collected containing 98.8% of 2,6-dinitro-3,4-dimethylphenol, which corresponds to a yield of 90.9%.

EXAMPLE 2

This example illustrates the alkylation stage of 3,4-disubstituted dinitrophenol.

5 g of tetrabutylammonium 2,6-dinitro-3,4-dimethylphenate and 50 g of 1,2-dichloroethane are loaded into a 50 ml flask equipped with a stirrer, a condenser and a thermometer.

The mixture is refluxed for 11 hours.

Then it is cooled down to 25° C., then washed successively with 20 g of 0.1N HCl, then three times with 17 g of 0.1M soda, then with 30 ml of 0.1N HCl and, finally, with 35 g of distilled water.

An organic phase is recovered which is dried over magnesium sulphate then evaporated under vacuum.

2.65 g of a yellow-orange coloured solid is collected containing 99% (determination by gas phase chromatography) of 2-(2,6-dinitro-3,4-dimethyl-phenoxy)-1-chloroethane.

The mother aqueous phases and those from washing are back-extracted at pH 1 with 130 g of 1,2-dichloroethane.

After drying and evaporation of the solvent, 0.15 g of an orange solid is collected containing 61.8% of 2,6-dinitro-3,4-dimethylphenol, 18.1% of 2-(2,6-dinitro-3,4-dimethylphenoxy)-1-chloroethane and 16.7% of tetrabutylammonium hydroxide, this product can be recycled as it is in a subsequent operation.

EXAMPLE 3

This example illustrates the alkylation stage of 3,4-disubstituted dinitrophenol.

5 of tetrabutylammonium 2,6-dinitro-3,4-dimethylphenate obtained by salification of 2,6-dinitro-3,4-dimethylphenol, then 1.78 g of benzyl bromide (namely 0.945 equivalent) and 10 g of toluene are loaded into a 50 ml flask equipped with a stirrer, a condenser and a thermometer.

The reaction medium is heated at 55 ±2° C. for 12 hours, then for 4 hours at 65° C.

The progress of the reaction is monitored by thin-layer chromatography.

After the total disappearance of the phenol, the reaction medium is concentrated under vacuum, the residue is then taken up in 70 g of 1,2-dichloroethane, then washed successively twice with 35 g of 1N HCl.

The organic phase, separated by decantation, is washed three times with 30 g of 0.1M soda, then with 25 g of 1N HCl, then again with 35 g of 0.1M soda, then with 35 g of 1M soda and finally with 30 g of distilled water.

The collected organic phase is dried over magnesium sulphate then evaporated under vacuum.

2.53 g of a yellow-orange solid is obtained constituted by 94% (determined by gas chromatography or GC) of 2,6-dinitro-3,4-dimethyl-phenyl-benzylether with a yield of 80%.

EXAMPLE 4

This example illustrates the amination stage.

2 g of 2-(2,6-dinitro-3,4-dimethyl-phenoxy)1-chloroethane with a purity of 99%, 6.1 g of amino-3-pentane and 3.1 g of methanol are loaded into a 25 ml three-necked flask equipped with a stirrer, a condenser and a thermometer.

The mixture is maintained at 45° C. for 8 hours, then at 55° C. for 9 hours.

Using thin-layer chromatography of an aliquot of the reaction medium the end of the reaction is detected by the disappearance of the ether.

The solvent and the excess of amine are then evaporated off under vacuum.

The residue obtained is taken up in dichloromethane then washed with 50 g of 0.1N HCl, then with 20 g of 1M soda and finally with 30 g of water until neutrality is achieved; then it is dried and evaporated to dryness under vacuum.

2.02 g of a yellow-orange solid is obtained containing 99.1% (determined by gas chromatography or GC) of 3,4-dimethyl-N(1-ethyl-propyl)-2,6-dinitrobenzenamine.

EXAMPLE 5

This example illustrates the amination stage.

2 g of 2,6-dinitro-3,4-dimethyl-phenyl-benzylether with a purity of 94%, 8.3 g of amino-3-pentane and 4 g of isopropanol are loaded into a 25 ml three-necked flask equipped with a stirrer, a condenser and a thermometer.

The mixture is maintained at 55° C. for 9 hours, then at 75° C. for 8 hours.

Using thin-layer chromatography of an aliquot of the reaction medium the end of the reaction is detected by the disappearance of the ether.

The solvent and the excess of amine are then evaporated off under vacuum.

The residue obtained is taken up in isopropylether; the suspension obtained is filtered and the filtrate is washed with 50 g of 1M soda, then with 20 g of water until neutrality is achieved before being dried then evaporated to dryness at 95° C. under vacuum of 7 mm Hg.

1.0 g of a mixture of 3,4-dimethyl-N(1-ethyl-propyl)-2,6-dinitrobenzenamine and of 3,4-dimethyl-2,6-dinitrophenol is obtained which is separated by thin layer chromatography.

The quantity of 3,4-dimethyl-N(1-ethyl-propyl)-2,6-dinitrobenzenamine thus collected is 0.4 g.

EXAMPLE 6

This example illustrates the O-alkylation stage by an oxirane of a 3,4-disubstituted dinitrophenol.

20 g of 2,6-dinitro-3,4-dimethylphenol of 98.6% purity, 10 g of toluene and 0.2 g of pyridine are loaded into a 100 ml reaction vessel equipped with magnetic stirring, a manometer and a bursting disk (40 bars). The reaction medium is cooled down to 10° C. and 6.54 g of propylene oxide is poured in. The reaction vessel is closed and subjected to a nitrogen pressure of 2–3 bars.

The reaction medium is heated at 120° C. for 3 hours.

After cooling down to 30° C., decompression is carried out,

After the toluene has been evaporated off, 26.4 g of a brown oil is collected composed of 94.01% of 2-propanol-1-(2,6-dinitro-3,4-dimethylphenoxy) and 1.51% of (2,6-dinitro-3,4-dimethylphenoxy)-propanoxy-propanol.

EXAMPLE 7

This example illustrates the O-alkylation stage by an oxirane of a 3,4-disubstituted dinitrophenol.

20 g of 2,6-dinitro-3,4-dimethylphenol of 98.06% purity, 10 g of xylene and 0.1 g of pyridine are loaded into a 100 ml reaction vessel equipped with magnetic stirring, a manometer and a bursting disk (40 bars). The reaction medium is cooled down to 10° C. and 5 g of ethylene oxide is poured in. The reaction vessel is closed and subjected to a nitrogen pressure of 2–3 bars.

The reaction medium is heated at 120° C. for 7 hours.

After cooling down to 30° C., decompression is carried out.

After the xylene has been evaporated off, 24.07 g of a brown solid is collected composed of 92.8% of ethanol-2-(2,6-dinitro-3,4-dimethylphenoxy) and of 1.73% of (2,6-dinitro-3,4-dimethylphenoxy)-ethoxy-ethanol.

EXAMPLE 8

This example illustrates the amination stage of 1-(2,6-dinitro-3,4-dimethylphenoxy)2-propanol.

40 g of 2-propanol-1-(2,6-dinitro-3,4-dimethyl-phenoxy) of 96.2% purity and of 2.53% of the diaddition product, 141.4 g of amino-3-pentane at 44.7% in water and 0.8 g of $CaCl_2, 6H_2O$ are loaded into a 100 ml three-necked flask equipped with a magnetic stirrer, a condenser (−10° C.) and a thermometer.

The mixture is maintained under reflux (83° C.) for 8 hours.

Using thin-layer chromatography on an aliquot of the reaction medium, the end of the reaction is detected by the disappearance of the ether.

The excess water/amine azeotrope is distilled, the residue is washed at 80° C. with 100 g of water saturated with NaCl, then taken up in dichloromethane, then evaporated under vacuum.

37.15 g of an orange solid is obtained constituted by 92.38% (determined by GC) of N-(1-ethylpropyl)-2,6-dinitro-3,4-dimethyl-benzenamine.

EXAMPLE 9

This example illustrates the amination stage of 1-(2,6-dinitro-3,4-dimethylphenoxy)2-ethanol.

24 g of ethanol-2-(2,6-dinitro-3,4-dimethylphenoxy) of 92.8% purity and of 1.73% of (2,6-dinitro-3,4-dimethylphenoxy)ethoxy-ethanol, 65.03 g of amino-3-pentane at 60% in water and 0.5 g of $CaCl_2,6H_2O$ are loaded into a 100 ml three-necked flask equipped with a magnetic stirrer, a condenser (−10° C.) and a thermometer.

The mixture is maintained under reflux (84° C.) for 7 hours.

By using thin-layer chromatography on an aliquot of the reaction medium, the end of the reaction is detected by the disappearance of the ether.

The excess water/amine azeotrope is distilled, the residue obtained is taken up in xylene then washed with 30 g of 5% HCl, then with 40 g of 5% soda and finally with 100 g of water until neutrality is achieved, then evaporated under vacuum.

23.4 g of an orange solid is obtained constituted by 92.31% (determined by GC) of N-(1-ethylpropyl)-2,6-dinitro-3,4-dimethyl-benzenamine.

We claim:

1. In a process for the preparation of 3,4-disubstituted dinitroanilines of formula

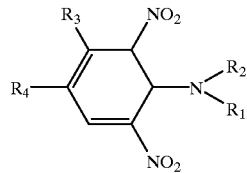

in which
  $R_1$ and $R_2$, which are identical or different from one another, are selected from the group consisting of the hydrogen atom, the $C_1$ to $C_6$ saturated, linear and branched alkyl radicals, the $C_2$ to $C_6$ linear and branched alkylene radicals, the cyclopropyl radical and the chloroethyl radical,
  $R_3$ and $R_4$, which are identical or different from one another, are selected from the group consisting of the chlorine atom, the amino group, the $C_1$ to $C_3$ lower alkyl radicals and the trifluoromethyl radical,
said process comprising successively, selecting a 3,4-disubstituted phenol corresponding to the contemplated 3,4-disubstituted dinitroaniline, the dinitration of the 3,4-disubstituted phenol, the O-alkylation of the dinitrated 3,4-disubstituted phenol and the amination of the thus obtained 3,4-disubstituted 2,6-dinitro-alkoxybenzene,
the improvement according to which
  the dinitration of the 3,4-disubstituted phenol providing the dinitrated 3,4-disubstituted phenol is carried out in a reaction medium containing a slight excess of nitrating agent, a quantity of protons from 2 to 7 equivalents with respect to the phenol and a catalyst selected from the group consisting of the soluble salts of the transition metals indicated in columns IV to XII of the Periodic Chart of the Elements,
  the O-alkylation of the dinitrated 3,4-disubstituted phenol is carried out using an alkylating agent selected from the group consisting of linear and branched alkyl mono-halides having at least 3 carbon atoms, of linear and branched alkyl polyhalides having at least 2 carbon atoms, of polyalkoxy-haloalkyl ethers represented by the formula $(RO)_nR'X$ in which X represents a hydrogen atom, chlorine, bromine or iodine atom and in which R and R', independently of one another, represent a methyl, ethyl or propyl radical, n being such that the number of carbon atoms in the alkylating agent is $\geq 2$, of ethylene oxide, of propylene oxide and of the compounds whose structure corresponds to the formula

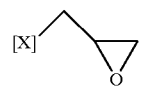

which represents epihalohydrins when X represents Cl or Br, glycidol when X represents OH, glycidyl ethers when X represents OR, R being an aliphatic chain with at most 12 carbon atoms, and oxirane when X is an aliphatic chain R having 1 to 12 carbon atoms.

2. Process according to claim 1, wherein the catalyst is selected from the group consisting of the soluble salts of $Fe_{III}$, $Fe_{II}$, $Zn_{II}$ and $Cu_{II}$ ions.

3. Process according to claim 1 wherein the linear and branched alkyl monohalides having at least 3 carbon atoms as well as the linear and branched alkyl polyhalides having at least 2 carbon atoms contain a saturated ring or at least one unsaturation and wherein the polyalkoxy-haloalkyl ethers of formula $(RO)_nR'X$ are selected from the group consisting of the chloromethyl-polymethoxy ethers and the chloromethyl-polyethoxy ethers.

4. Process according to claim 1, wherein the proportion of catalyst relative to the phenol is from 1 to 50 per thousand.

5. Process according to claim 4 wherein the proportion of catalyst relative to the phenol is from 5 to 30 per thousand.

6. Process according to claim 1, wherein the quantity of protons present in the nitrating medium is from 2.4 to 6 equivalents with respect to the phenol.

7. Process according to claim 6, wherein the quantity of protons present in the nitrating medium is from 2.6 to 2.9 equivalents with respect to the phenol.

8. Process according to claim 7, wherein the protons present in the nitrating medium are provided by an inorganic or by an organic acid called co-acid and selected from the group consisting of the hydrochloric, the hydrobromic, the sulphuric, the phosphoric acids and the lower carboxylic acids.

9. Process according to claim 8, wherein the lower carboxylic acid is selected from the group consisting of the acetic, the propionic and the oxalic acid.

10. Process according to claim 1, wherein the alkylating agent used during the O-alkylation stage is selected from the group consisting of the alkyl monohalides represented by the formula $C_nH_{2n-1}X$ in which X is a chlorine, bromine or iodine atom and n is $\geq 3$, and of the alkyl polyhalides represented by the formula $C_nH_{2n-m}X_{2+m}$ in which X is an atom of chlorine, bromine or iodine and $n \geq 2$ with $0 \leq m \leq 2n$.

11. Process according to claim 10, wherein the alkylating agent is selected from the group consisting of, as alkyl monohalides, the n-propyl, isopropyl, n-butyl, sec-butyl, isobutyl, tert-butyl, n-pentyl, sec-amyl, 3-pentyl, neopentyl, hexyl, isohexyl, cyclohexyl, cyclopropyl, benzyl, allyl and polyalkoxyalkyl halides, with a methoxy, ethoxy or propanoxy radical as alkoxylated chain and, as alkyl polyhalides, the dichloroethane, the dibromoethane, the 1,2- and the 1,3-dichloropropane.

12. Process according to claim 1, wherein the amination stage is carried out in an inert solvent selected from the group consisting of the aromatic solvents and alcohols by reacting, at atmospheric pressure or under 3 to 5 atmospheres and at a temperature between 30° C. and the reflux temperature of the medium, the O-alkylated dinitrated 3,4-substituted phenol with an excess of a secondary or primary amine selected from the group consisting of amino-3-pentane, N,N-diethylamine, N,N-dipropylamine, N-ethyl,N-butylamine, N-propyl,N-methyl-cyclopropylamine, N-(2-chloroethyl),N-propylamine, N-propyl,N-2-methyl-2-propenyl-amine, N-ethyl-,N-2-methyl-2-propenyl-amine.

* * * * *